(12) United States Patent
Cuthbertson et al.

(10) Patent No.: US 8,568,689 B1
(45) Date of Patent: Oct. 29, 2013

(54) UPAR-TARGETING CONTRAST AGENTS

(75) Inventors: Alan Cuthbertson, Nycoveien (NO); Bente E. Arbo, Nycoveien (NO)

(73) Assignee: GE Healthcare AS, Oslo (NO)

( * ) Notice: Subject to any disclaimer, the term of this patent is extended or adjusted under 35 U.S.C. 154(b) by 1607 days.

(21) Appl. No.: 11/576,193

(22) PCT Filed: Sep. 28, 2005

(86) PCT No.: PCT/NO2005/000362
§ 371 (c)(1),
(2), (4) Date: Mar. 28, 2007

(87) PCT Pub. No.: WO2006/036071
PCT Pub. Date: Apr. 6, 2006

(30) Foreign Application Priority Data

Sep. 29, 2004 (NO) .................................. 20044139

(51) Int. Cl.
*A61K 51/00* (2006.01)
*A61M 36/14* (2006.01)

(52) U.S. Cl.
USPC ....... 424/1.69; 424/1.11; 424/1.65; 424/1.81; 424/1.85; 424/1.89; 424/9.1

(58) Field of Classification Search
USPC ........... 424/1.11, 1.65, 1.69, 1.81, 1.85, 1.89, 424/9.1, 9.2, 9.3, 9.4, 9.5, 9.6, 9.7, 9.8; 530/300, 324–328; 514/1, 1.1
See application file for complete search history.

(56) References Cited

U.S. PATENT DOCUMENTS

| | | | |
|---|---|---|---|
| 6,277,818 B1 | 8/2001 | Mazar et al. | |
| 6,514,710 B1 | 2/2003 | Jones et al. | |
| 6,896,870 B1 * | 5/2005 | Mazar et al. | 424/1.69 |
| 7,026,282 B1 * | 4/2006 | Ploug et al. | 530/328 |

FOREIGN PATENT DOCUMENTS

| | | |
|---|---|---|
| WO | 94/22464 | 10/1994 |
| WO | WO 98/57665 | 12/1998 |
| WO | 00/01802 | 1/2000 |
| WO | 01/25410 | 4/2001 |
| WO | 2005/084715 | 9/2005 |

OTHER PUBLICATIONS

Poethko, et.al. "Two-step methodology for high-yield routine rahalogenation of peptides: 18F-labeled RGD and octreotide analogs" The Journal of Nuclear Medicine, vol. 45, No. 5 May 2004 pp. 892-902.
Ploug, M. et.al. "Peptide-derived antagonists of the urokinase receptor. Affinity maturation by combinatorial chemistry, identification of functional epitopes, and inhibitory effect on cancer cell intravasation" Biochemistry, vol. 40, 2001 pp. 12157-12168.
Plough, M. "Photoaffinity labeling of the human receptor for urokinase-type plasminogen activator using a decapeptide antagonist. Evidence for a composite ligand-binding site and a short interdomain separation" Biochemistry, American Chemical Society., Easton, PA, vol. 37, No. 11. Mar. 17, 1998 pp. 3612-3622.
PCT/NO2005/000362 ISR & Written Opinion dated Sep. 2006.
PCT/NO2005/000362 International Preliminary Exam Report dated Mar. 14, 2007.

* cited by examiner

*Primary Examiner* — D L Jones
(74) *Attorney, Agent, or Firm* — Yonggang Ji

(57) ABSTRACT

The invention relates to contrast agents for detection of the Urokinase Plasminogen Activator Receptor (uPAR). More specifically the invention relates to contrast agents comprising a peptidic vector binding to the uPAR, labelled with an imageable moiety.

16 Claims, No Drawings

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: cyclohexylalanine

<400> SEQUENCE: 1

Asp Xaa Phe Ser Arg Tyr Leu Trp Ser
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: cyclohexylalanine

<400> SEQUENCE: 2

Thr Xaa Phe Ser Arg Tyr Leu Trp Ser
1               5
```

<210> SEQ ID NO 3
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: cyclohexylalanine

<400> SEQUENCE: 3

Gly Gly Asp Xaa Phe Ser Arg Tyr Leu Trp Ser
1               5                   10

<210> SEQ ID NO 4
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: cyclohexylalanine
<220> FEATURE:
<221> NAME/KEY: MISC_FEATURE
<222> LOCATION: (19)..(19)
<223> OTHER INFORMATION: cyclohexylalanine

<400> SEQUENCE: 4

Asp Xaa Phe Ser Arg Tyr Leu Trp Ser Ala Lys Ser Trp Leu Tyr Arg
1               5                   10                  15

Ser Phe Xaa Asp
            20

<210> SEQ ID NO 5
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: cyclohexylalanine

<400> SEQUENCE: 5

Asp Xaa Phe Ser Arg Tyr Leu Trp Ser Gly
1               5                   10

UPAR-TARGETING CONTRAST AGENTS

This application is a filing under 35 U.S.C. 371 of international application number PCT/NO2005/000362, filed Sep. 28, 2005, which claims priority to application number 20044139 filed Sep. 29, 2004, in Norway the entire disclosure of which is hereby incorporated by reference.

FIELD OF THE INVENTION

The present invention relates to contrast agents for detection of the Urokinase Plasminogen Activator Receptor (uPAR). More specifically the invention relates to contrast agents comprising a peptidic vector binding to the uPAR, labelled with an imageable moiety. The contrast agents may be used to identify sites where uPAR is expressed to diagnose diseases associated with this receptor.

BACKGROUND OF INVENTION

The interaction of the urokinase-type plasminogen activator (uPA) with cell surfaces is exclusively mediated by its glycolipid-anchored receptor (uPAR) to which uPA binds with high affinity.

uPAR is localised to the outer layer of the cell membranes via glycosyl phosphatidylinositol linkage (GPI anchor). It is a cysteine-rich heavily glycosylated protein composed of three homologous domains. uPA is composed of the catalytic C-terminal serine protease domain and a modular N-terminal part including a growth factor-like domain (GFD; aa 1-49) and a kringle domain (aa 50-135). The interaction between uPA and uPAR is primarily mediated by residues 19-31 of the GFD of uPA.

Since proteolytic degradation of the extracellular matrix has an established role in tumour invasion and metastasis, uPAR represents a potential target for diagnostic contrast agents. uPAR appears to be up-regulated in vivo in most human carcinomas examined to date, specifically, in the tumour cells themselves, in tumour-associated endothelial cells undergoing angiogenesis and in macrophages. uPAR overexpression in cancer patients is present in advanced disease and has been correlated with poor prognosis in numerous human carcinomas. The fact that uPAR expression is upregulated only in pathological states involving extracellular matrix remodelling and cell motility such as cancer makes it an attractive marker for diagnosis.

WO 01/25410 describes diagnostically or therapeutically labelled uPAR-targeting proteins and peptides. The peptide or protein comprises at least 38 amino acid residues, including residues 13-30 of the uPAR binding site of uPA.

U.S. Pat. No. 6,277,818 describes uPAR-targeting cyclic peptide compounds that may be conjugated with a diagnostic label. The peptides are based on the amino acid residues 20-30 of uPA.

U.S. Pat. No. 6,514,710 is also directed to cyclic peptides having affinity for uPAR. The peptides may carry a detectable label. The peptide comprises 11 amino acids joined by a linking unit.

Ploug et al. in Biochemistry 2001, 40, 12457-12168 describes uPAR targeting peptides but not in the context of imaging, including amino acid sequences as described in the present document.

The efficient targeting and imaging of uPAR demands a selective high-affinity vector that is chemically robust and stable. These stringent conditions are met by the contrast agents of the invention.

SUMMARY OF THE INVENTION

In view of the needs of the art the present invention provides contrast agents for detection of the Urokinase Plasminogen Activator Receptor (uPAR). More specifically the invention relates to contrast agent comprising a peptide sequence binding to the uPAR with high affinity, labelled with an imageable moiety. Ploug discloses e.g. a uPAR targeting peptide with the sequence X-Phe-X—X-Tyr-Leu-Trp-Ser, wherein standard abbreviations for the amino acids are used and wherein X denotes an amino acid selected from a group of 25 amino acids.

DETAILED DESCRIPTION OF THE INVENTION

Viewed from a first aspect the invention provides a uPAR targeting contrast agent of formula Ia, $$Z_1-W_1-X_0-X_1\text{-Phe-}X_2-X_3-X_4\text{-Leu-Trp-}X_5-X_6-W_2-Z_2 \quad \text{(Ia)}$$

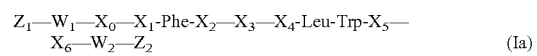

wherein, $X_0$ represents 1-5 amino acids, $X_1, X_2, X_3, X_4$ and $X_5$ independently represent one amino acid, Phe represents phenylalanine, Leu represents leucine, Trp represents tryptophan, $X_6$ represents 0 to 5 amino acids or is identified by formula (Ib), $$\beta\text{-Ala-Lys}(Z_1-W_1-X_0-X_1\text{-Phe-}X_2-X_3-X_4\text{-Leu-Trp-}X_5) \quad \text{(Ib)}$$

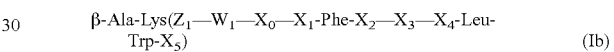

wherein the denotations are defined as for formula Ia, and wherein

β-Ala represents β-Alanine,

Lys represents lysine, and wherein $W_1$ and $W_2$ represent the same or different moiety, and are individually a spacer, a biomodifier or is absent, and at least one $Z_1$ or $Z_2$ is present representing an imageable moiety capable of detection either directly or indirectly in a diagnostic imaging procedure.

The amino acids $X_0, X_1, X_2, X_3, X_4, X_5$ and $X_6$ all represent natural or unnatural amino acids, and are preferably natural, except $X_1$ which is preferably unnatural. All amino acids are either in D or L form, with preferences as given below.

The $X_0-X_1\text{-Phe-}X_2-X_3-X_4\text{-Leu-Trp-}X_5-X_6$ component of the agent of formula Ia has affinity for uPAR and is herein after denoted a peptidic vector. The peptidic vector of the contrast agent has homology with the Growth Factor Domain of uPA but differs from uPAR targeting vectors of the prior art in that it does not comprise an amino acid sequence identical to an amino acid sequence found in human uPA.

$X_0$ represents 1 to 5, D or L amino acids. Preferably $X_0$ includes amino acids selected from the group of alanine (Ala), threonine (Thr), glycine (Gly), aspartic acid (Asp) and glutamic acid (Glu). The amino acids are preferably in the L form, except threonine which is preferably in the D form. Most preferably $X_0$ represents L-Asp, D-Thr or Gly-Gly-Asp.

$X_1$ preferably represents a β-cycloalkylalanine and is more preferably β-cyclopentylalanine, β-cyclohexylalanine (Cha) or β-cycloheptylalanine, and is most preferably β-cyclohexylalanine.

$X_2$ preferably represents serine (Ser) or alanine (Ala), more preferably serine and most preferably D-serine.

$X_3$ preferably represents arginine (Arg), or an arginine mimetic such as N-methylarginine (mArg), tyrosine (Tyr) or alanine, and more preferably D-arginine.

$X_4$ preferably represents tyrosine, alanine, leucine or cyclohexylalanine, more preferably tyrosine and most preferably L-tyrosine.

$X_5$ preferably represents serine, histidine (His), alanine, tyrosine or leucine, and more preferably L-serine or D-histidine.

$X_6$ preferably represents 0 to 5, D or L amino acids. Preferably $X_6$ includes amino acids selected from the group of glycine, aspartic acid, lysine, phenylalanine or β-alanine (β-Ala). Alternatively, $X_6$ comprises the group of formula (Ib)

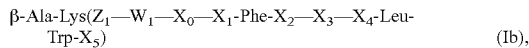

β-Ala-Lys($Z_1$—$W_1$—$X_0$—$X_1$-Phe-$X_2$—$X_3$—$X_4$-Leu-Trp-$X_5$) (Ib), wherein all symbols are as earlier defined and wherein the β-Ala of formula Ib is linked to $X_5$ of formula Ia. The peptide chain in brackets is linked via its $X_5$ to the ε-amino group of lysine. In this alternative the contrast agent will comprise a dimer synthesised on a modified lysine scaffold having its α-amino group prederivatized with β-alanine thus creating a pseudo symmetrical dimer with respect to the α-carbon atom of lysine. In this alternative, the dimer is preferably a homodimer, wherein the peptide sequences in the two monomers are the same. Most preferably $X_6$ is absent.

Surprisingly, it has been found that the $X_4$ and $X_5$ positions of the peptidic vector, wherein Ploug uses tyrosine and serine respectively, may be replaced with other amino acids as outlined above.

$W_1$ and $W_2$ individually represent a moiety acting as spacer, a biomodifier moiety or both, or is absent, and is preferably based on a monodisperse polyethylene glycol (PEG) building block comprising 1 to 10 units of said building block. $W_1$ or $W_2$ may also represent 1 to 10 amino acid residues preferably comprising glycine, lysine, aspartic acid, serine or aminohexanoic acid. More preferably, $W_1$ or $W_2$ comprises both amino acid residues and a PEG-based structure, such as 1-10 amino acid residues in combination with a PEG-based structure. Preferably, either $W_1$ or $W_2$ represent a biomodifier and in a preferred embodiment at least one of $W_1$ or $W_2$ represents a unit comprised of the monodisperse PEG-based structure, 17-amino-5-oxo-6-aza-3,9,12,15-tetraoxa-heptadecanoic acid of formula (II),

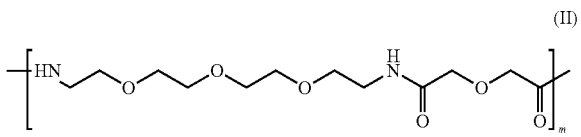

(II)

wherein m equals an integer from 1 to 10 and where the C-terminal end is an amide or acid moiety. As a biomodifier, $W_1$ or $W_2$ has the function of modifying the pharmacokinetics and blood clearance rates of the compounds. The biomodifier effects less uptake of the compounds in tissue i.e. muscle, liver etc. thus giving a better diagnostic image due to less background interference. The secretion is mainly through the kidneys which is a further advantage of the biomodifier.

As a biomodifier moiety $W_1$ or $W_2$ is preferably derived from glutaric and/or succinic acid and/or a PEG based unit, e.g. including the moiety of formula II. $W_1$ or $W_2$ can further act as a spacer, with biomodifier properties, linking the imageable moiety $Z_1$ or $Z_2$ to the peptidic vector. Other representative spacer elements include structural-type polysaccharides, storage-type polysaccharides, polyamino acids and methyl and ethyl esters thereof, and polypeptides, oligosaccharides and oligonucleotides, which may or may not contain enzyme cleavage sites. As a spacer moiety one role of $W_1$ or $W_2$ is to distance a relatively bulky imageable moiety from the receptor binding domain of the peptidic vector. Alternatively, in the simplest form $W_1$ or $W_2$ is a functional bond or comprises a functional group which permits facile conjugation of the imageable moiety to the peptidic vector, such groups include —$NR^a$—, $CO_2$, —N(C=S)—, —N(CO)—, —S, —O—, —O—$NH_2$ and —CHO wherein the $R^a$ group is independently H, $C_{1-10}$ alkyl, $C_{3-10}$ alkylaryl, $C_{2-10}$ alkoxyalkyl, $C_{1-10}$ hydroxyalkyl, $C_{1-10}$ halooalkyl and α-haloacetyl.

When $Z_1$ is absent and $W_1$ present, $W_1$ preferably has an N-terminal with a free amino group or an amino group comprising a metabolism inhibiting group. By the term metabolism inhibiting group is meant a biocompatible group which inhibits or suppresses in vivo metabolism of the peptide or amino acid at the amino terminus. Such groups are well known to those skilled in the art and are suitably selected from the group of acetyl, Boc, (tert-butyloxycarbonyl), Fmoc (fluorenylmethoxycarbonyl), benzyloxycarbonyl, trifluoroacetyl and allyloxycarbonyl. Preferred metabolism inhibiting groups are acetyl and benzyloxycarbonyl. When $Z_2$ and $W_2$ are absent, the C-terminal of the peptidic vector is preferably an amide or carboxylic group, and preferably an amide group. Also when $Z_2$ is absent, and $W_2$ is present comprising amino acids, $W_2$ preferably ends with an amide or carboxylic group, and more preferably an amide group.

The contrast agent of the invention preferably comprises a linear peptide, meaning that there are no bridges between any of the amino acids, or between amino acids and other moieties of the agent that generate a cyclic structure. There are hence preferably no sulphide, thioether bridges or other bridges forming cyclic peptide structures. The contrast agent preferably comprises a maximum of 20 amino acids.

In a preferred embodiment the peptidic vector represented by $X_0$—$X_1$-Phe-$X_2$—$X_3$—$X_4$-Leu-Trp-$X_5$—$X_6$ of formula Ia comprises the sequence: $X_0$-Cha-Phe-Ser-Arg-Tyr-Leu-Trp-Ser, such that the contrast agent has the formula $Z_1$—$W_1$—$X_0$-Cha-Phe-Ser-Arg-Tyr-Leu-Trp-Ser-$X_6$—$W_2$—$Z_2$, wherein the denotations are as earlier defined.

More preferably the peptidic vector comprises the sequence: Asp-Cha-Phe-Ser-Arg-Tyr-Leu-Trp-Ser, or Thr-Cha-Phe-Ser-Arg-Tyr-Leu-Trp-Ser, wherein italic font denotes D amino acids and wherein $X_6$ is absent.

One example of a contrast agent of the invention is: $Z_1$—$W_1$-Gly-Gly-Asp-Cha-Phe-Ser-Arg-Tyr-Leu-Trp-Ser-$NH_2$ wherein $Z_1$ and $W_1$ are as earlier defined, and wherein $X_6$, $W_2$ and $Z_2$ are absent, and wherein the C-terminal is an amide group.

At least one of $Z_1$ and $Z_2$ is present and represents an imageable moiety. Z is hereinafter used to denote either $Z_1$ or $Z_2$. Z can be any imageable moiety. The nature of Z will depend on the imaging modality utilised in the diagnosis. A wide range of moieties suitable for detection in in vivo imaging are known from e.g. WO 98/47541, the content of which is incorporated by reference.

Z is a moiety capable of detection either directly or indirectly in an in vivo diagnostic imaging procedure, such as radio or SPECT, PET, MR, x-ray, ultrasound or optical imaging. Z comprises e.g. a moiety which emits or may be caused to emit detectable radiation (eg. by radioactive decay, fluorescence excitation, spin resonance excitation, etc.), a moiety which affects local electromagnetic fields (e.g. paramagnetic, superparamagnetic, ferrimagnetic or ferromagnetic species), a moiety which absorbs, emits or scatters radiation energy (e.g. chromophores, particles (including gas or liquid containing vesicles), a heavy element and compounds thereof, etc.), and a moiety which generates a detectable substance (eg. gas microbubble generators).

The imageable moiety Z may be represented by an entity M and a moiety $Y_1$, wherein M represents metal ions, paramagnetic metals, metal radio-nuclides, heavy metals and heavy metal oxides. The moiety $Y_1$ must be able to carry one or several moieties M. By carrying is meant any form of association between the moiety $Y_1$ and M such as a chemical bond, e.g. covalent bond or electrovalent or ionic bonds or by absorption or any other type of association, and preferably M is chelated by a chelating moiety $Y_1$.

Imaging modalities and imageable moieties Z are described in more detail hereinafter:

In a first embodiment of this aspect, Z comprises one or more moieties M useful in the radio and SPECT imaging modality such as a radioactive metal ion or a gamma-emitting radioactive halogen, optionally carried by a moiety $Y_1$. Preferably M is a gamma emitter with low or no alpha- and beta-emission and with a half-life of more than one hour. Preferred groups M are the radionuclides $^{67}Ga$, $^{111}In$, $^{123}I$, $^{125}I$, $^{131}I$, $^{81m}Kr$, $^{99}Mo$, $^{99m}Tc$, $^{201}Tl$ and $^{133}Xe$. Most preferred is $^{99m}Tc$.

M can further be represented by the following isotopes or isotope pairs: $^{47}Sc_{21}$; $^{141}Ce_{58}$; $^{188}Re_{75}$; $^{177}Lu_{71}$; $^{199}Au_{79}$; $^{47}Sc_{21}$; $^{131}I_{53}$; $^{67}Cu_{29}$; $^{131}I_{53}$ and $^{123}I_{53}$; $^{188}Re_{75}$ and $^{99m}Tc_{43}$; $^{90}Y_{39}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

When M denotes a metallic radionuclide for radio or SPECT imaging then $Y_1$ preferably denotes a chelating agent suitable for forming a stable chelate with M. Such chelating agents are well known from the state of art and typical examples of such chelating agents are described in Table I of WO 01/77145.

Particularly preferred are chelating agents $Y_1$ of formula (III):

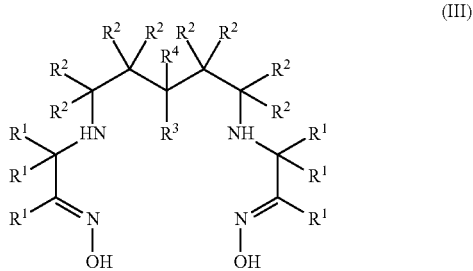

wherein:

each $R^1$, $R^2$, $R^3$ and $R^4$ is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring.

More particularly preferred are chelating agents $Y_1$ of formula (III) where $R^1$, $R^2$ and $R^3$ are hydrogen or methyl groups and $R^4$ is an alkyl or an alkylamine group. More preferably $Y_1$ is the chelate of formula (IV), herein denoted cPN216, and most preferably the imaging moiety M is $^{99m}Tc$. The star denotes a possible linking site.

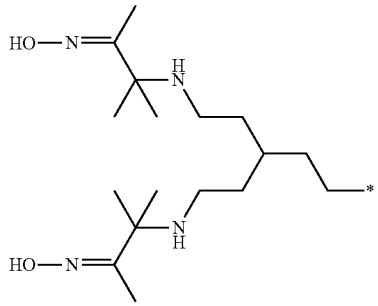

Other preferred chelating agents are of formula (V)

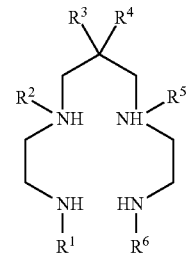

wherein R1-R6 independently represent H, alkyl, aryl or a combination thereof, where R1-R6 groups contain one or more functional moieties such that the chelate can be conjugated to $W_1$ or $W_2$ of formula (Ia). Suitable functional moieties are e.g. alkylamine, alkylsulphide, alkoxy alkyl carboxylate, arylamine, aryl sulphide or alfa-haloacetyl.

If Z represent a gamma-emitting radioactive halogen such as $^{123}I$, $^{125}I$, $^{131}I$ and $^{77}Br$, wherein $^{125}I$ is preferred, it may be covalently linked to $W_1$ or $W_2$ by a substitution or addition reaction well known from the state of art, or alternatively to $X_0$ or $X_6$ if $W_1$ or $W_2$ is absent, or directly to $X_5$ if $X_6$ is absent.

In a second embodiment, the compound of formula (Ia) comprises a moiety Z useful in the PET imaging modality. Z then comprises a radioemitter with positron-emitting properties, preferably a positron-emitting radioactive non-metal. Preferred groups Z comprise either of the positronemitters $^{11}C$, $^{18}F$, $^{13}N$, $^{15}O$, $^{77}F$, $^{75}Br$, $^{76}Br$ and $^{124}I$. $^{18}F$ is specifically preferred. Suitable metallic positron-emitters are $^{64}Cu$, $^{48}V$, $^{52}Fe$, $^{55}Co$, $^{94m}Tc$, $^{68}Ga$ or $^{82}Rb$, $^{68}Ga$ being preferred, which can be chelated with a chelating agent $Y_1$.

Non-metal radionuclides such as those comprising $^{18}F$ may be covalently linked to the moiety $W_1$ or $W_2$ when present or alternatively to $X_0$, $X_5$ or $X_6$ by a substitution or addition reaction well known from the state of art.

When Z is an $^{18}F$-labelled aldehyde, thiol or aminooxygroup then $W_1$ or $W_2$ preferably has a functional group comprising an alpha-halo acetyl moiety, an aldehyde or an aminooxy group. Thiol coupling chemistry and aldehyde and aminooxy coupling chemistry, $^{18}F$-synthons and labelled peptides prepared using this chemistry are described in WO 03/080544 and WO 04/080492, the content of which is incorporated herein by reference. Alternatively, $^{18}F$ may be introduced by other moieties comprising $^{18}F$ such as e.g. $^{18}F$-fluorobenzaldehyde. The linking site, $W_1$, $W_2$, $X_0$, $X_5$ or $X_6$ would then preferably comprise an aminooxy group.

When M denotes a metallic positron-emitter for PET imaging then $Y_1$ denotes a chelating agent suitable for forming a stable chelate with M. Such chelating agents are well known from the state of art and typical examples of such chelating agents are described in Table I of WO 01/77145 and in the previous embodiment directed to radio and SPECT imaging.

In a preferred embodiment $Y_1$ is the DOTA chelating agent and M is $^{68}$Ga which can be readily introduced in to the chelate using microwave chemistry.

In a third embodiment, Z comprises a moiety $Y_1$ carrying one or more moieties M useful in the MR imaging modality. M here denotes a paramagnetic metal, suitable such metal ions include: Gd(III), Mn(II), Cu(II), Cr(III), Fe(III), Co(II), Er(II), Ni(II), Eu(III) or Dy(III). Gd(III), Dy(III), Fe(III) and Mn(II) are particularly preferred. $Y_1$ denotes a chelating agent, in particular a chelating agent such as acyclic or cyclic polyaminocarboxylates (e.g. DTPA, DTPA-BMA, DOTA and DO3A) as described e.g. in U.S. Pat. No. 4,647,447 and WO 86/02841. M may also denote metal oxides such as superparamagnetic, ferrimagnetic or ferromagnetic species which are adsorbed by or bound to $Y_1$, e.g. such that $Y_1$ function as a coating to the metal oxide. Metal oxides for use as MR contrast agents are described e.g. in U.S. Pat. No. 6,230,777 which is hereby incorporated by reference.

In a fourth embodiment Z represents an imageable moiety useful in the X-ray imaging modality. Z here comprises a heavy metal such as tungsten, gold and bismuth preferably in the form of oxides. Z can also be represented by iodinated aryl derivatives particularly well known as X-ray contrast agents, e.g. Iopamiron™ and Omnipaque™. These agents can be linked via their acid or amine functions to the peptidic vector of formula (Ia), optionally via $W_1$ or $W_2$.

In a further embodiment the compound of formula (Ia) comprises Z in the form of gas-filled microvesicles. Such ultrasound imaging agents can be utilised in the imaging of receptors e.g. when they are functionalised for binding to a peptide as described in the state of art e.g. in WO98/18500.

In a sixth, and preferred, embodiment of the present invention the moiety Z of formula (Ia) may be any moiety capable of detection either directly or indirectly in an optical imaging procedure. The detectable moiety can be a light scatterer (e.g. a coloured or uncoloured particle), a light absorber or a light emitter. More preferably Z is represented by a dye such as a chromophore or a fluorescent compound. The moiety Z can be any dye that interacts with light in the electromagnetic spectrum with wavelengths from the ultraviolet light to the near-infrared. In a preferred version Z has fluorescent properties.

Preferred organic dye moieties include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes and bis(S,O-dithiolene) complexes. From the fluorescent dyes the group of cyanine dyes is preferred. Even more preferred are the groups of carbacyanines, oxacyanines, thiacyanines and azacyanines. The groups of Cy5- and Cy7-dyes are the most preferred fluorescent dyes, and these can be linked to the peptidic vector by a N-hydroxysuccinimide ester (NHS-ester). Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots).

Preferred dyes are selected from the group of carbacyanines, and even more preferred are the carbacyanine dyes of the indole type. Preferred dyes of this type are illustrated by formula VI:

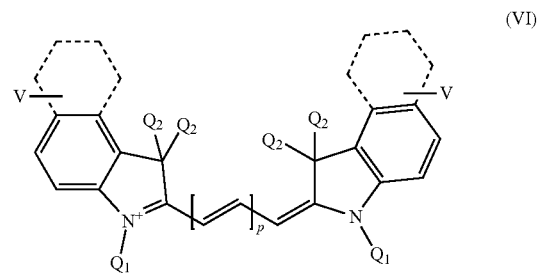

(VI)

wherein the $Q_1$ groups are the same or different and are substituted or unsubstituted lower alkyl groups, e.g. $C_1$ to $C_6$ alkyl groups which are optionally substituted. The alkyl groups are substituted e.g. with carboxy, sulphonic acid, amine, ammonium or ester groups, such as heterocyclic ester groups (e.g. NHS-ester). The $Q_2$ groups are the same or different and are lower alkyl groups, such as $C_1$ to $C_6$ alkyls, preferably methyl groups, optionally substituted with e.g. carboxy or sulphonic acid groups.

Optional aromatic groups are indicated by dotted lines, to include both structures comprising condensed benzo rings and condensed naphtho rings. Either rings are substituted or unsubstituted. The rings may be substituted with a group V selected from sulphonic acid groups, carboxylic groups, hydroxyl groups, alkyl(sulphoalkyl)amino groups, bis(sulphoalkyl)amino groups, sulphoalkoxy groups, sulphoalkylsulphonyl group, alkyl or substituted alkyl or sulphoalkylamino groups. p is a positive integer 1, 2, 3 or 4. Preferably, the cyanine dye is a pentamethine or a heptamethine dye with carbon-bridges of 5 and 7 carbon atoms, respectively.

$Q_1$, $Q_2$ and V are potential linking sites for the linking of the dye to the peptidic vector, optionally via $W_1$ and/or $W_2$, the $Q_1$ and V group being preferred linking sites. In a preferred aspect one $Q_1$ group is linked to the peptidic vector while the other $Q_1$ group is an optionally substituted lower alkyl group.

Viewed from a second aspect the invention provides uPAR targeting compounds of formula (VII)

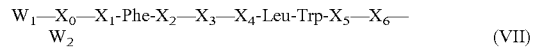

(VII)

wherein the denotations are defined as for formula Ia, and wherein at least one of $W_1$ and $W_2$ is present and represents a biomodifier as described. The compounds of formula VII may be linked to an imageable moiety, as described in the first aspect, or may have other uses, such as in therapy.

The compounds of the present invention can be synthesised using the known methods of chemical synthesis but particularly useful is the solid-phase methodology of Merrifield employing an automated peptide synthesiser (J. Am. Chem. Soc., 85: 2149 (1964)). Typically, the desired sequences are assembled by solid-phase peptide synthesis. Standard procedures for the synthesis strategy employed for the examples of this invention are described in E. Atherton & R. C. Sheppard, "Solid phase peptide synthesis: a practical approach", 1989, IRL Press, Oxford.

For example, resins with a variety of acid-labile linker groups are used that will yield peptides with a C-terminal acid, amine or amide. The amino protecting group is then removed and the second amino acid in the sequence is coupled using a suitable condensation reagent. Amino acids with semi-permanent amino protecting groups and permanent protecting groups for the functional side chains are employed. Amino-deprotection and coupling cycles are then repeated in alternating steps until the sequence of interest is assembled.

Alternatively, the peptides can be synthesised through solution peptide synthesis methods known in the art, either in a step-wise manner from the carboxyl terminus and/or through the application of segment condensation or ligation methods, employing comprehensive or minimal protection strategies. Combined solution-solid phase segment condensation approaches can also be applied.

Generally, the reactive side-chain groups present (for example amino, hydroxyl, guanidino and carboxyl groups) will be protected during overall synthesis as indicated above. A wide choice of protecting groups for amino acids is known (see, e.g., Greene, T. W. & Wuts, P. G. M. (1991) Protective groups in organic synthesis, John Wiley & Sons, New York). Amino protecting groups which may be employed include 9-fluorenylmethoxycarbonyl (Fmoc) and t-butyloxycarbonyl (Boc). Side-chain protecting groups which may be employed include t-butyl (tBu), trityl (Trt), Boc, and 2,2,5,7,8-pentamethylchroman-6-sulfonyl (Pmc). It will be appreciated that a wide range of other such groups are known in the art.

Finally the permanent side-chain protecting groups are removed and the peptide is cleaved from the resin, usually simultaneously through treatment with a suitable acidic reagent, e.g. trifluoroacetic acid (TFA).

$W_1$ and/or $W_2$ can be conjugated to the peptidic vector using known methods of chemical synthesis. Particularly useful is the direct conjugation of $W_1$ and/or $W_2$ to the peptidic vector by amide bond formation, as for preparation of the peptidic vector. Alternatively, a nucleophile substitution reaction where a leaving group on the peptide N-terminus is replaced by a nucleophilic group on $W_1$ and/or $W_2$ may be used. Such a leaving group may be a bromide attached in alpha position to a carbonyl group, and such a nucleophile may be nitrogen.

Z can be conjugated directly to the peptide using the same methods as for the conjugation of $W_1$ and/or $W_2$ to the peptidic vector. In the case where Z is attached to the peptide via $W_1$ or $W_2$ any methods of chemical synthesis may be used in the conjugation of Z and $W_1$ or $W_2$. Particularly useful is the automatically coupling of Z yielding e.g. an amide bond between the peptide and the imagable moiety. Methods for linking a reporter moiety to a peptide is well known in the art and will depend on the reporter chosen and on which spacers are used.

The peptidic vector and the contrast agent may be purified using high performance liquid chromatography (HPLC) and characterised by mass spectrometry and analytical HPLC.

The requirements of the compounds of the invention to function as efficient contrast agents of the uPA/uPAR system is that on the one hand the peptidic vector should have a high affinity for the receptor, and on the other hand that the vector should "stay" on the receptor as long as necessary. Thus the contrast agent/uPAR system should preferably exhibit slow dissociation kinetics (the so-called "off-rate"), which may conveniently be expressed as the dissociation rate constant $K_{diss}$. The contrast agents of the invention have been found to have greatly improved receptor-binding kinetics. Based thereon, the contrast agents of the invention which are especially preferred have a dissociation rate constant ($K_{diss}$) relative to the Growth Factor Domain of uPA (GFD) of preferably <50, more preferably <20, even more preferably <10, and most preferably <1.

The contrast agents of the invention are preferably able to inhibit the binding of uPA to cell-surface uPAR. The contrast agent of the invention is preferably equipotent with diisopropyl fluorophosphates inactivated uPA. The parameter $IC_{50}$ gives the concentration where 50% of the uPA are competed off. Preferred contrast agents of the invention have an $IC_{50}$<50 nM, preferably <25 nM, more preferably <10 nM, and even more preferably <3 nM.

Contrast agents according to the invention are preferably used to identify sites where uPAR is expressed to diagnose diseases associated with up-regulation of the receptor. The receptor is preferably more than 50% more abundant in the diseased tissue than in surrounding tissue. More preferably the receptor is more than two times more abundant in diseased tissue than in surrounding tissue. Even more preferably, the receptor is more than 5 times more abundant in diseased tissue than in surrounding tissue.

Viewed from a further aspect the invention provides a method for detecting the presence of uPAR on the surface of a cell, in a tissue, in an organ or in a biological sample suspected of overexpressing uPAR due to a pathological state. The method comprises the steps of a) contacting the cell, tissue, organ or biological sample with the contrast agent of the invention and b) detecting the presence of the imageable moiety associated with the cell, tissue, organ or sample. In this method both the contacting and the detection may be conducted in vitro, alternatively the contacting is in vivo and the detection in vitro, preferably the contacting and the detection is in vivo.

A preferred method includes generating an image of a human or animal body by diagnostic imaging involving administering a contrast agent as described to said body, e.g. into the vascular system, and generating an image of at least a part of said body, to which said contrast agent has distributed.

Viewed from a still further aspect the invention provides a method of generating enhanced images of a human or animal body by imaging, previously administered with a contrast agent composition comprising a contrast agent as defined, which method comprises generating an image of at least part of said body.

The new contrast agents of the invention may be used as contrast agents in any imaging modality, depending on the imageable moiety chosen. Use of the contrast agents in diagnostic imaging is hence an aspect of the invention. A preferred aspect is contrast agents as described for use in imaging of and diagnosing of different forms of cancer and metastasis, e.g. breast, skin, colorectal, pancreatic, prostate, lung or ovarian cancer. Alternatively, the contrast agent may be used for detection of diseases where activated macrophages are present such as vulnerable plaque in atherosclerosis.

The present invention also provides a pharmaceutical composition comprising an effective amount, e.g. an amount effective for enhancing image contrast in in vivo imaging of a contrast agent of the invention, or a salt thereof, together with one or more pharmaceutically acceptable adjuvants, excipients or diluents.

Viewed from a further aspect the invention provides the use of a contrast agent of the invention for the manufacture of a contrast enhancing agent for use in a method of diagnosis involving administration of said contrast enhancing agent to a human or animal body and generation of an image of at least part of said body.

The present invention will now be further illustrated by way of non-limiting examples in which the following abbreviations are used:
BAEEG: Bis-(aminoethyl)ethylene glycol
Boc: t-butyloxycarbonyl
Cy: Cyanine
DEG: Diethyleneglycol
DMF: N,N-dimethylformamide
Fmoc: 9-fluorenylmethoxycarbonyl
HATU: 2-(7-Aza-1H-benzotriazole-1-yl)-1,1,3,3-tetramethyluronium hexafluorophosphate
HPLC: High performance liquid chromatography
Krytofix 222: 4,7,13,16,21,24-hexaoxa-1,10-diazabicyclo-(8,8,8)hexacosane
LC: Liquid chromatography
MS: Mass spectroscopy
NHS: N-hydroxysuccinimide
NMM: N-methylmorpholine
PEG: Polyethylene glycol
PBS: Phosphate buffer
Pmc: 2,2,5,7,8-pentamethylchroman-6-sulfonyl
PyAOP: (7-Azabenzotriazole-1-yloxy)tripyrrolidinophosphonium hexafluorophosphate
Rink Amide MBHA resin: 4-methylbenzhydrylamin linked to a polystyrene matrix
RP-HPLC: Reversed phase HPLC
RT: Room temperature
Sep-Pak: Separation column with a C18-resin
TFA: Trifluoroacetic acid
TIS: Triisoproylsilane Example 1

Cy5(bis-SO$_3$)-Thr-Cha-Phe-Ser-Arg-Tyr-Leu-Trp-Ser-OH (2)

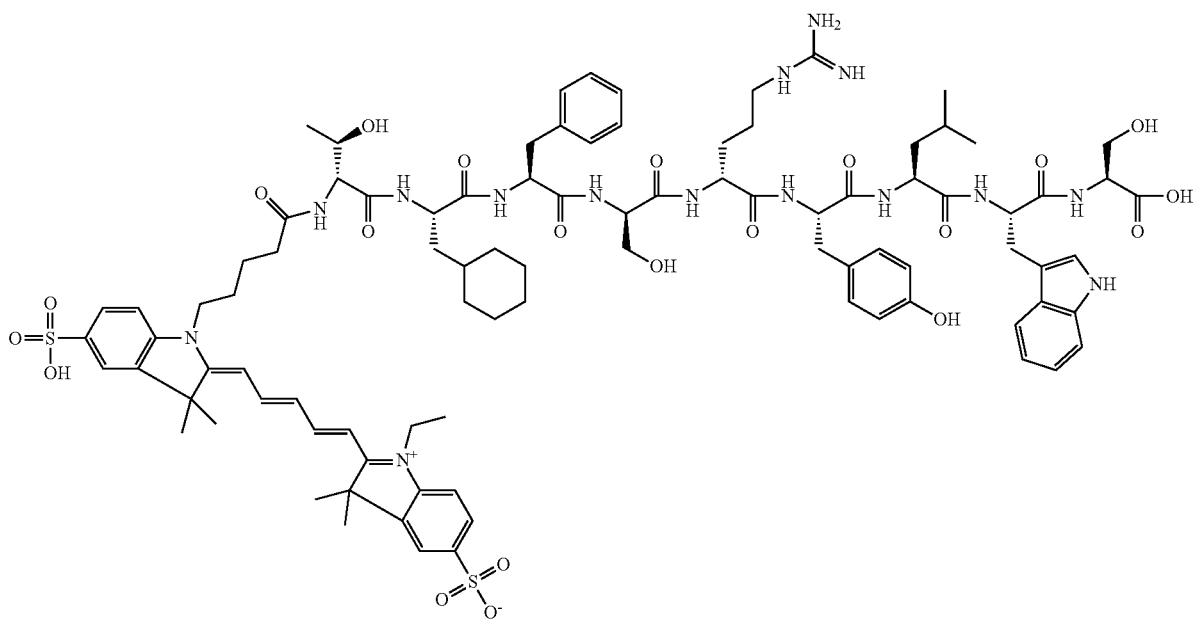

Synthesis of H-Thr-Cha-Phe-Ser-Arg-Tyr-Leu-Trp-Ser-OH (1)

The peptide corresponding to the above sequence was synthesized by standard solid-phase peptide chemistry.

Conjugation of Cy5(bis SO$_3$) Mono NHS ester to peptide (1)

Cy5(bis SO$_3$) mono NHS ester (1.18 mg, 0.0017 mmol) was dissolved in DMF and peptide (1) (2 mg, 0.0015 mmol) was added as a solid to the solution, followed by the addition of NMM (0.55 μl, 0.005 mmol). The reaction vessel was wrapped in foil and placed on a shaker apparatus for 16 hours. The desired product was confirmed by electrospray MS: [M+H]$^+$ of product expected at 1850.85 m/z, found at 1850.9 m/z.

Example 2

Cy5(bis-SO$_3$)-Gly-Gly-Asp-Cha-Phe-Ser-Arg-Tyr-Leu-Trp-Ser-NH$_2$ (3).

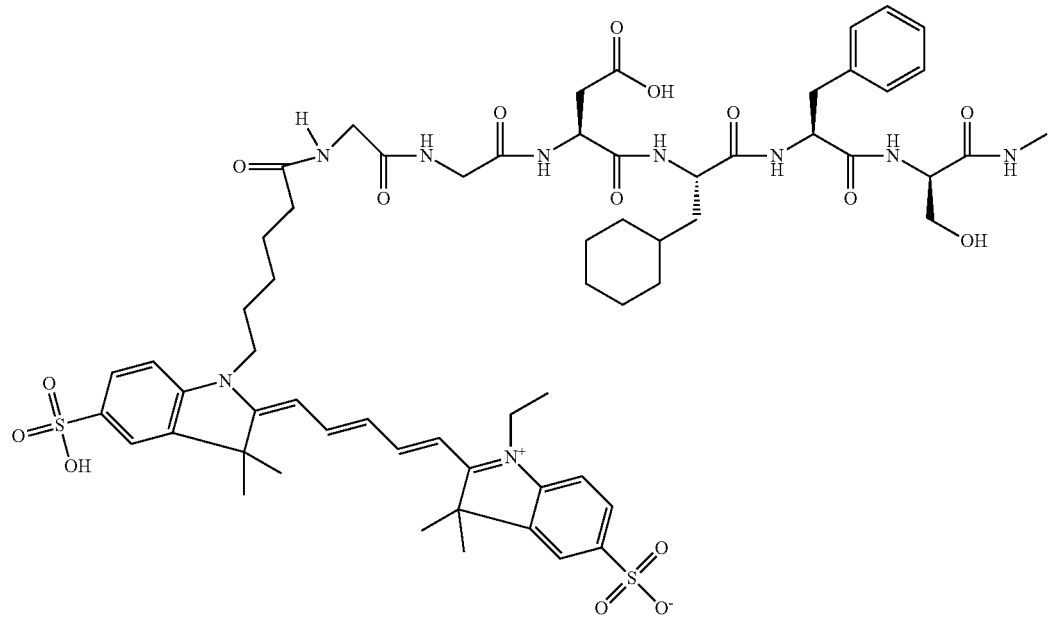

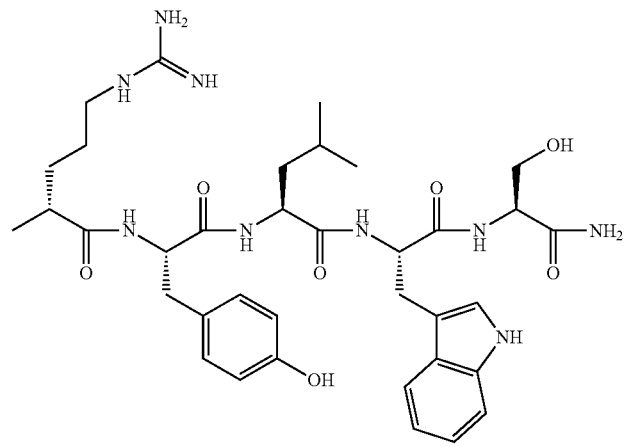

Synthesis of Cy5(bis-SO$_3$)-Gly-Gly-Asp-Cha-Phe-Ser-Arg-Tyr-Leu-Trp-Ser-NH$_2$ (3)

The amino acids in the above sequence were assembled by standard solid-phase peptide chemistry. Cy5(bis SO$_3$) mono NHS ester (0.5 eq) was then dissolved in DMF and added to the H-Gly-Gly-Asp(OtBu)-Cha-Phe-Ser(tBu)-Arg(Pmc)-Tyr(tBu)-Leu-Trp(Boc)-Ser(tBu)-Rink Amide MBHA resin (1 eq) followed by addition of NMM (3 eq). The reaction vessel was wrapped in foil and placed on a shaker apparatus for 16 hours. The Cy5 dye conjugated peptide was de-protected and cleaved from the resin by treatment with TFA containing 2.5% water and 2.5% TIS for 1 hour. The desired product was confirmed by electrospray MS: [M+H]$^+$ of product expected at 1977.88 m/z, found at 1977.8 m/z.

Example 3

Cy5(bis-SO$_3$)-Asp-Cha-Phe-Ser-Arg-Tyr-Leu-Trp-Ser-βAla-Lys(Cy5(bis-SO$_3$)-Asp-Cha-Phe-Ser-Arg-Tyr-Leu-Trp-Ser)-NH$_2$ (5)

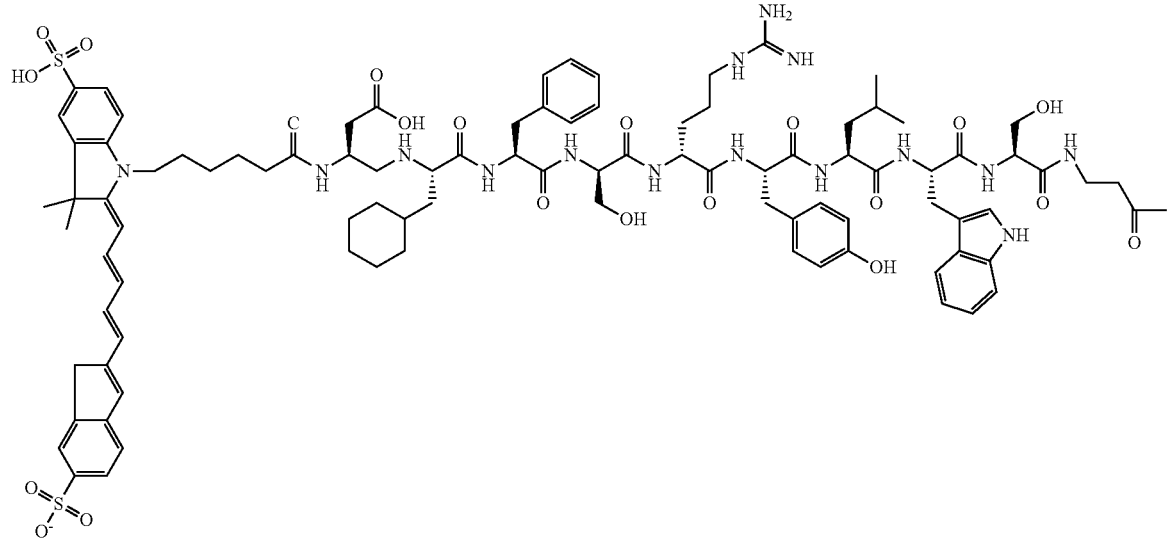

5

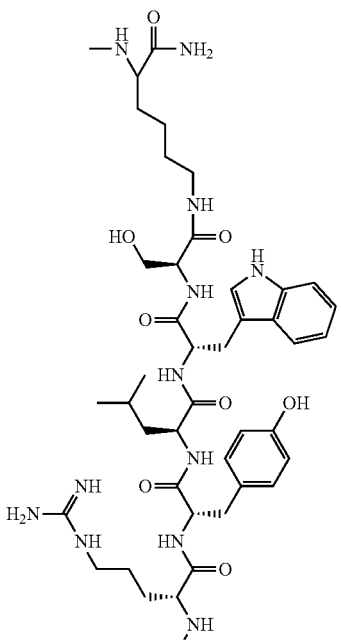

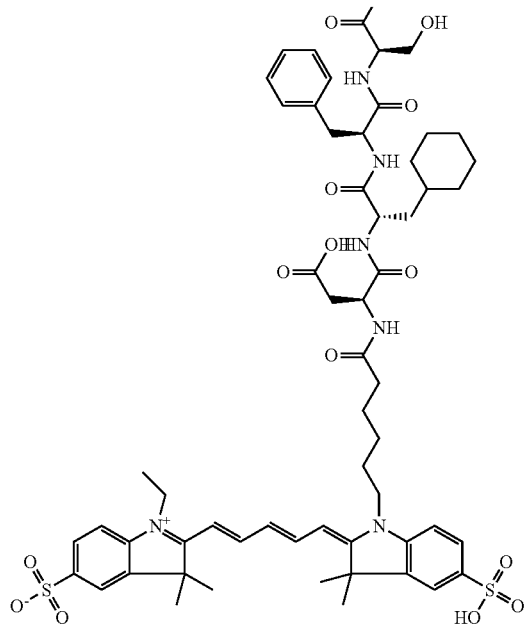

Synthesis of H-Asp-Cha-Phe-Ser-Arg-Tyr-Leu-Trp-Ser-βAla-Lys(H-Asp-Cha-Phe-Ser-Arg-Tyr-Leu-Trp-Ser)-NH₂ (4)

The peptide corresponding to the above sequence was assembled by standard solid-phase peptide chemistry.

Conjugation of Cy5(bis SO₃) mono NHS ester to peptide (4)

The Cy5(bis SO₃) mono NHS ester (2.2 eq) is dissolved in DMF and peptide (4) (1 eq) is added as a solid to the solution followed by the addition of NMM (3 eq). The reaction vessel is wrapped in foil and placed on a shaker apparatus for 24 hours to afford the desired bis-conjugated product. The product is analyzed by RP-HPLC and electrospray-MS.

Example 4

N-(4-18F-fluorobenzylidene)aminooxyacetyl-PEG(4)-diglycoloyl-Asp-Cha-Phe-Ser-Arg-Tyr-Leu-Trp-Ser-NH₂ (8)    8

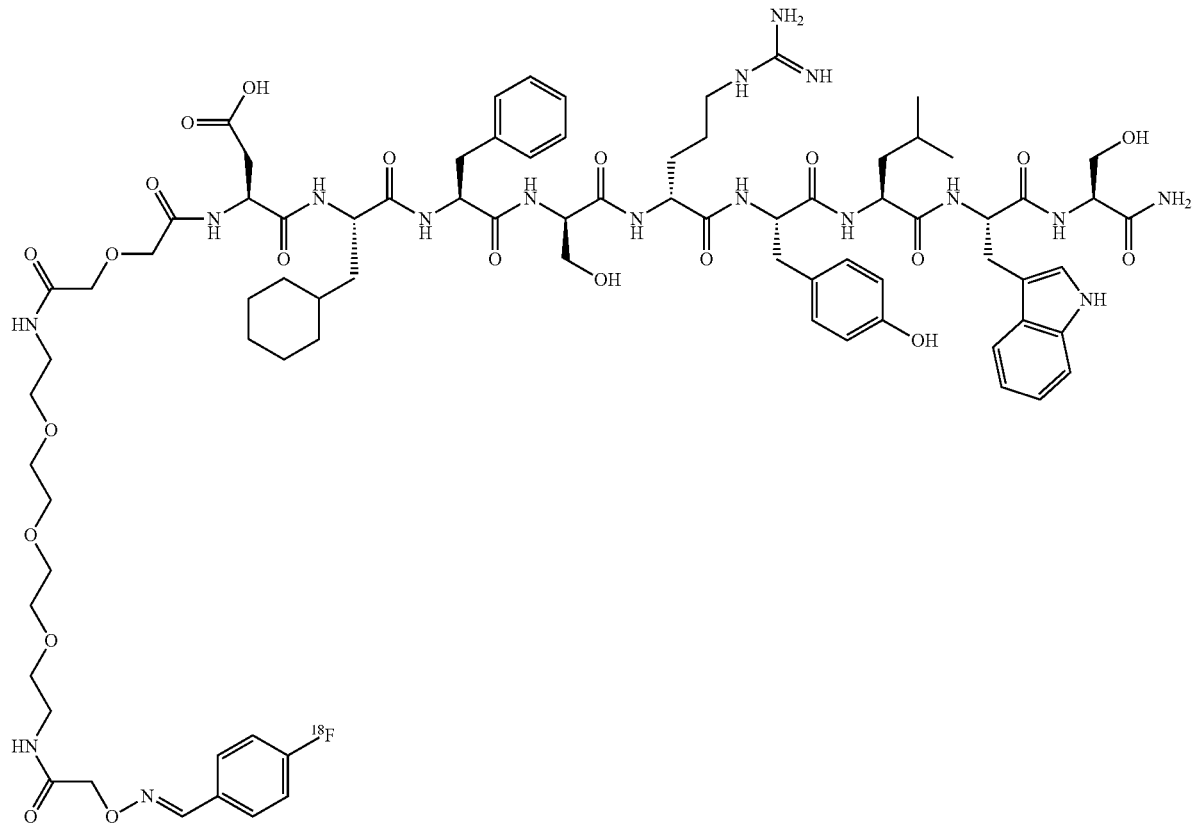

Synthesis of N-Boc-aminooxyacetyl-PEG(4)-diglycoloyl-Asp-Cha-Phe-Ser-Arg-Tyr-Leu-Trp-Ser-NH (7)

Boc-aminooxyacetyl-PEG(4)-diglycolic acid can be prepared by a skilled artisan using an active ester of Boc-aminooxyacetic acid and reacting it with the corresponding amino-PEG(4)-diglycolic acid. The obtained product Boc-aminooxyacetyl-PEG(4)-diglycolic acid (1.4 eq) and PyAOP (1.2 eq) is dissolved in DMF. NMM (2 eq, 200 µL) is added and the mixture is stirred for 5 min. A solution of peptide (6) (1 eq) and NMM (4 eq) in DMF is added and the reaction mixture is stirred for 30 min. DMF is evaporated in vacuo, and the product is purified using preparative RP-HPLC. The fractions containing the desired product is adjusted to pH 5 using 0.3% ammonia ($NH_3$)/water prior to lyophilisation in order to prevent removal of the Boc protecting group. The product is analyzed by PR-HPLC and electrospray-MS.

18F Labelling of Peptide (7)

$^{18}$F-Fluoride is azeotropically dried in the presence of Kryptofix 222 (5 mg in 0.5 ml ACN) and potassium carbonate (50 µl of 0.1 M solution) by heating to 110° C. under a flow of nitrogen for 20 min. During this time, 3×0.5 ml ACN is added and removed.

The mixture is cooled to <40° C. and trimethylammonium benzaldehyde triflate, synthesised according to the procedure described by Haka et al in J. Labelled Cpds.& Radiopharms 1989 27(7) 823, (1 mg in 0.4 ml dimethylsulfoxide) is added. The reaction vessel is sealed and heated to 90° C. for 15 min to effect labelling. The crude 4-18F-fluorobenzaldehyde solution is then cooled to room temperature. Meanwhile, peptide (7) (6 mg) is treated with 5% water in TFA (200 µl) for 5 min at room temperature to remove the Boc-protecting group. The solvents are removed in vacuo. The Boc-deprotected peptide is redissolved in 0.1M ammoniumacetate solution (pH4, 0.4 ml) and combined with the crude 4-18F-fluorobenzaldehyde solution in the reaction vessel. The vessel is sealed and heated to 70° C. for 15 min to effect conjugation. After cooling to room temperature, the crude conjugate is purified by prep HPLC. The fraction containing the desired conjugate is diluted with 10 ml water and loaded onto a C18 Sep-Pak (pre-prepared by washing sequentially with 10 ml ethanol and 20 ml water). The Sep-Pak is rinsed with 10 ml water, then eluted with 2 ml ethanol. The ethanol is removed in vacuo and the product (8) is formulated in PBS.

Example 5

Acetyl-PEG(4)-diglycoloyl-Asp-Cha-Phe-Ser-Arg-Tyr-Leu-Trp-Ser-Gly-BAEEG-Glut-cPN216 (10)

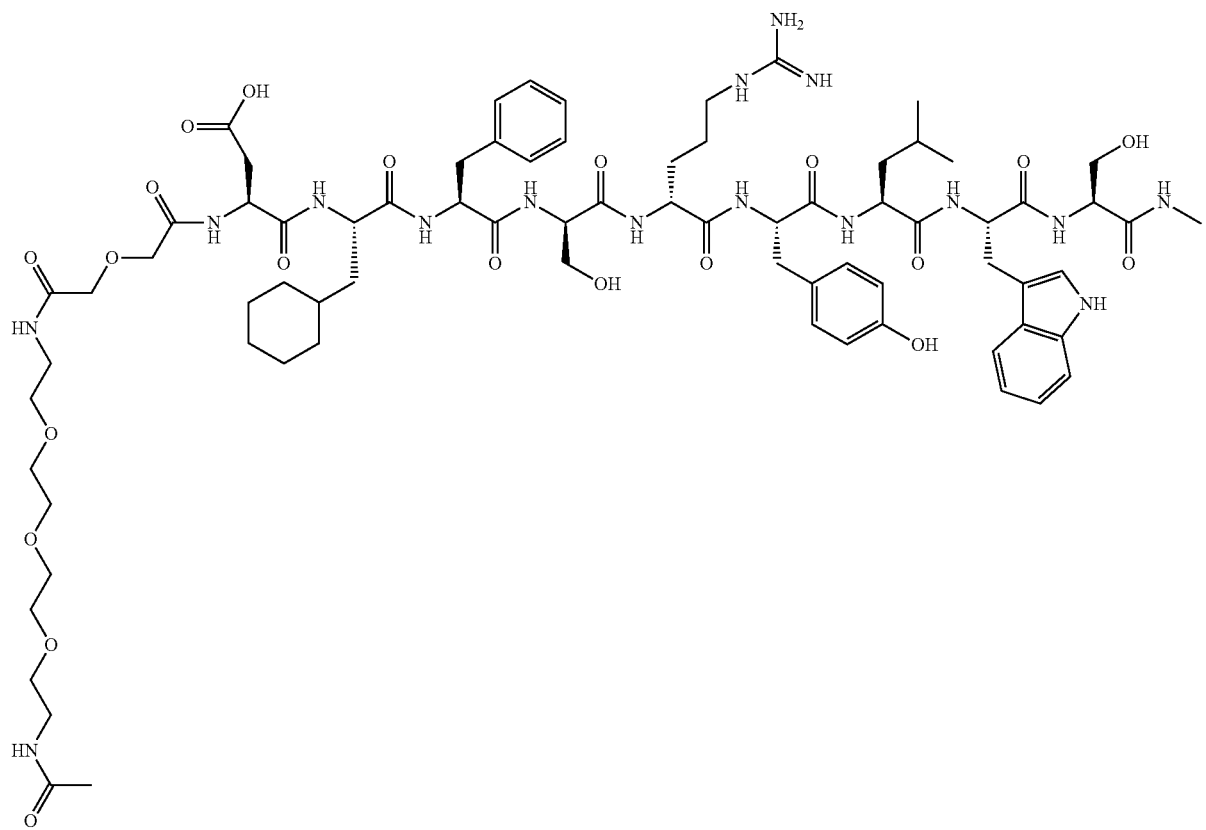

10

-continued

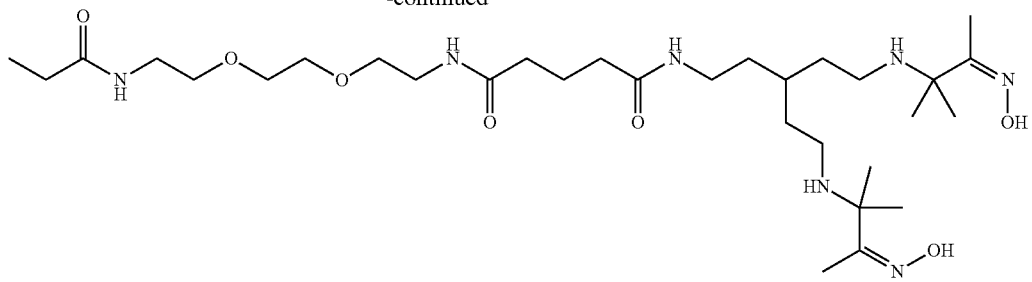

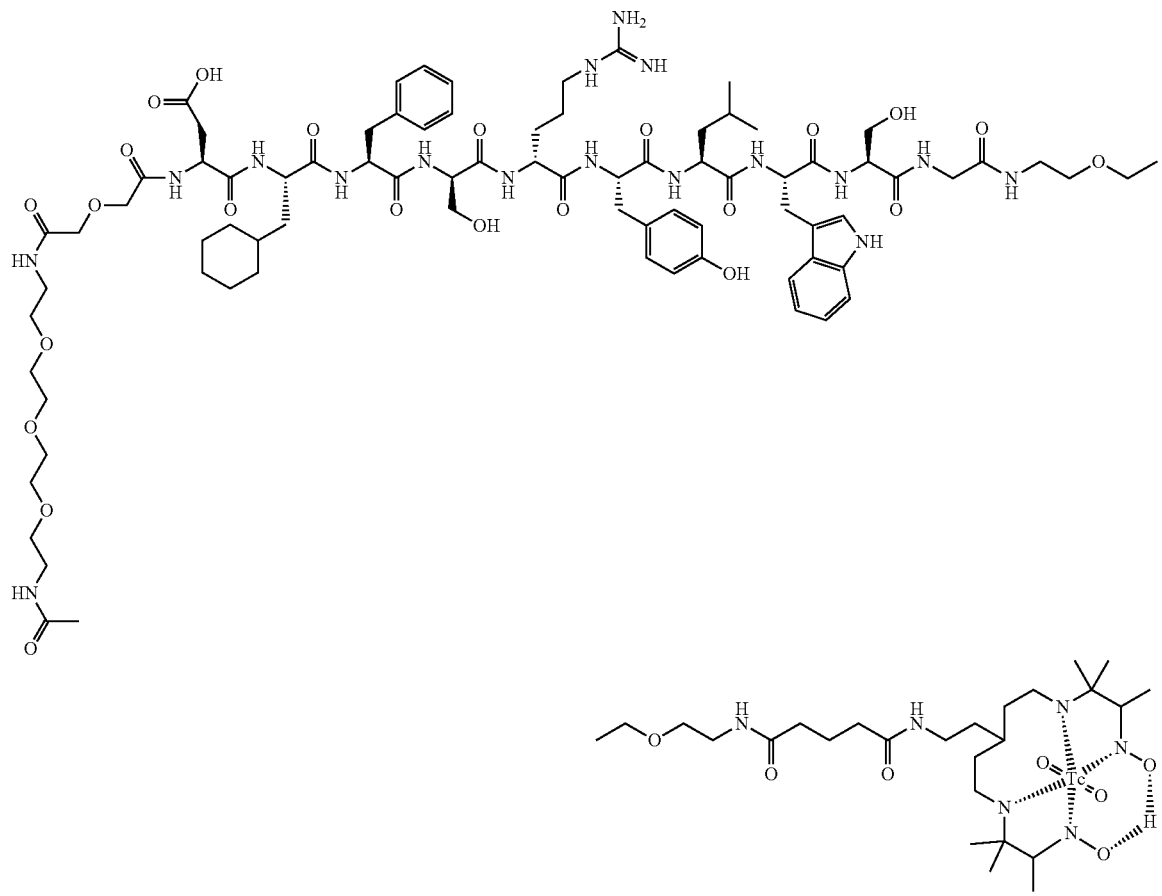

Synthesis of Acetyl-PEG(4)-diglycoloyl-Asp-Cha-Phe-Ser-Arg-Tyr-Leu-Trp-Ser-Gly-BAEEG-NH₂ (9)

The peptidyl resin corresponding to the above sequence is synthesized by standard solid-phase peptide chemistry. Acetyl-PEG(4)-diglycolic acid (5 eq) and PyAOP (4.5 eq) is dissolved in DMF. NMM (10 eq, 200 µL) is added and the mixture is stirred for min. The mixture is then added to the peptide resin pre-swollen in DMF and the reaction is continued over night. The peptide is then de-protected and cleaved from the resin using TFA containing 2.5% water and 2.5% TIS for 1 hour. The product is analyzed by RP-HPLC and electrospray-MS.

Conjugation of cPN216 to Peptide (9).

Peptide (9) (1 eq) is dissolved in DMF and cPN216-glutaryl-tetrafluorothiophenyl ester (2 eq) is added followed by NMM (3 eq). After stirring over night the reaction mixture is worked up by removing the solvent under reduced pressure and the product (10) is purified by preparative RP-HPLC. The product is analyzed by RP-HPLC and electrospray-MS.

[99m]Tc-labelling of peptide (10)

Peptide (10) (0.1 mg) is reconstituted in saline or methanol (0.1 ml) and transferred into a freeze dried Toolbox kit of excipients. The Toolbox kit, designed to provide generic radio labelling conditions for amine based chelates, contained stannous chloride dehydrate (16 µg), methylene diphosphonic acid (25 µg), sodium hydrogen carbonate (4500 µg), sodium carbonate (600 µg), sodium para-aminobenzoate (200 µg), Kit pH=9.2. Sodium Pertechnetate ($^{99m}$Tc) injection (2.1 GBq) in saline (3 ml) is then added, the kit is inverted a few times to dissolve the contents and is then left to incubate at room temperature for 15-20 min. A sample is analyzed immediately by HPLC and ITLC and the 99mTc-labelled peptide (11) is to be administered to the trial subject between 1-3 hours after reconstitution of the kit.
Example 6
Gadolinium(II) complex of acetyl-Asp-Cha-Phe-Ser-Arg-Tyr-Leu-Trp-Ser-Gly-BAEG-Glut-DOTA (15)
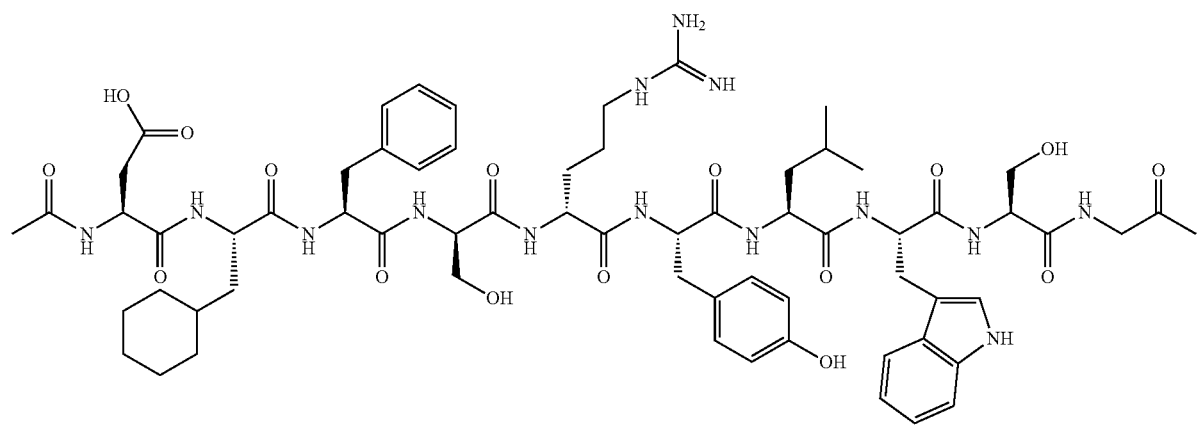
14
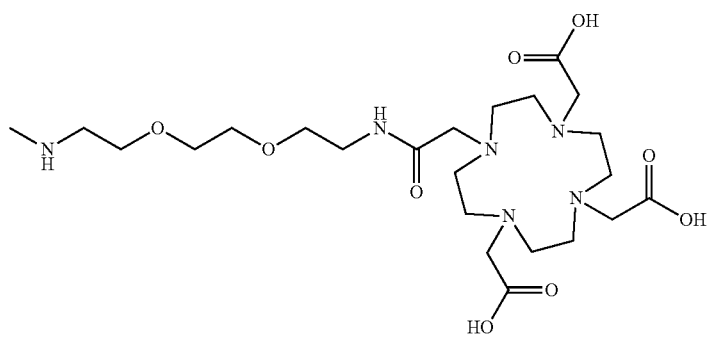
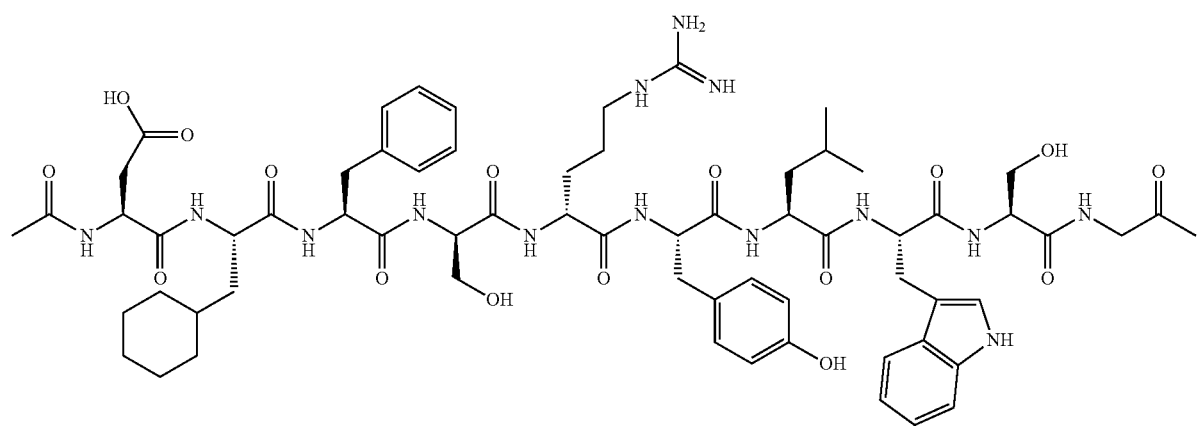
15

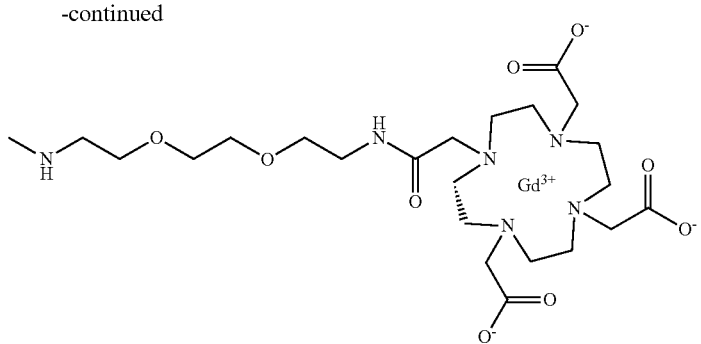

Synthesis of Acetyl-Asp-Cha-Phe-Ser-Arg-Tyr-Leu-Trp-Ser-Gly-DEG-NH₂ (12)

The peptide corresponding to the above sequence is synthesized by standard solid-phase peptide chemistry.

Synthesis of Tri-tBu-DOTA (13)

Tri-tBu-DO3A (1,4,7,10-tetraazacyclododecane-N,N',N"-triacetic acid, tri-tert-butyl ester, 10 mmol) and bromoacetic acid (10 mmol) was dissolved in MeOH (50 ml). $K_2CO_3$ (30 mmol) dissolved in water (50 ml) was added (pH 11 in the MeOH/water mixture) and the reaction was stirred for 24 hours and then heated at 40 degrees for another 24 hours. The crude product was purified by RP-HPLC (Phenomenex Luna micron, C18, 250×21.2 mm, gradient 5-50% B over 40 min at 10 ml/min). The desired product was confirmed by electrospray-MS: $[M+Na]^+$ of product expected at 595.4 m/z, found at $[M+Na]^+$ 595.3 m/z and by $^1$H-NMR at 80 degrees.

Synthesis of DOTA-Conjugated Peptide (14)

Tri-tBu-DOTA (13) (1,4,7,10-tetraazacyclododecane-N,N',N",N'"-tetraacetic acid, tri-tert-butyl ester 1 eq) is activated with HATU (1 eq) in DMF in the presence of and NMM (3 eq) for 5 min. The mixture is added to peptide (12) and the reaction is continued over night. The solvent is removed in vacuo and the product is tBu-deprotected in TFA containing 5% water. The product is purified by RP-HPLC and analyzed by RP-HPLC and electrospray-MS.

Complexation with Gd(III)

The DOTA-conjugated peptide (14) (1 eq) is reacted with $GdCl_3$ (1 eq) in an aqueous solution at pH 6.5 at RT. Uncomplexed Gd(III) is removed by centrifugation of the solution at basic pH. The product (15) is isolated by lyophilization.

---

The invention claimed is:

1. A uPAR imaging agent of formula Ia,

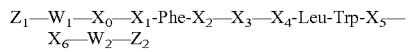
(Ia)

wherein, $X_0$ represents 1-5 amino acids, $X_1$, $X_2$, $X_3$, $X_4$ and $X_5$ independently represent one amino acid, Phe represents phenylalanine, Leu represents leucine, Trp represents tryptophan, $X_6$ represents 0 to 5 amino acids or is identified by formula (Ib),

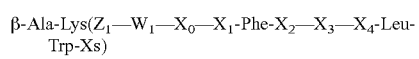
(Ib)

wherein the denotations are defined as for formula Ia, and wherein

β-Ala represents β-Alanine,

Lys represents lysine,

β-Ala of formula Ib is linked to $X_5$ of formula Ia, and wherein $W_1$ and $W_2$ are independently absent, a monodisperse polyethylene glycol (PEG) building block comprising 1 to 10 units of said building block, or 1 to 10 amino acid residues or combinations thereof;

$Z_1$ and $Z_2$ are independently absent or a Z group;

Z is an imageable moiety capable of detection either directly or indirectly in in vivo diagnostic imaging;

with the proviso that at least one of $W_1$ and $W_2$ is present and at least one of $Z_1$ and $Z_2$ is present.

2. An imaging agent as claimed in claim 1 wherein $X_0$ represents 1 to 5 amino acids selected from the group of alanine, threonine, glycine, aspartic acid and glutamic acid.

3. An imaging agent as claimed in claim 1 wherein $X_1$ represents a β-cycloalkylalanine.

4. An imaging agent as claimed in claim 1 wherein $X_2$ represents serine or alanine.

5. An imaging agent as claimed in claim 1 wherein $X_3$ represents arginine, tyrosine or alanine.

6. An imaging agent as claimed in claim 1 wherein $X_4$ represents tyrosine, alanine, leucine or cyclohexylalanine.

7. An imaging agent as claimed in claim 1 wherein $X_5$ represents serine, histidine, alanine, tyrosine or leucine.

8. An imaging agent as claimed in claim 1 wherein $X_6$ comprises amino acids selected from the group of glycine, aspartic acid, lysine, phenylalanine or β-alanine or is absent.

9. An imaging agent as claimed in claim 1 comprising the peptide sequence $Z_1$—$W_1$—$X_0$-Cha-Phe-Ser-Arg-Tyr-Leu-Trp-Ser-$X_6$—$W_2$—$Z_2$, wherein Cha represents cyclohexylalanine, Ser represents serine, Arg represents arginine, and Tyr represents tyrosine.

10. An imaging agent of claim 1 wherein Z is selected from the group consisting of a moiety detectable in radio, SPECT, PET, x-ray, MR, ultrasound or optical imaging.

11. An imaging agent as claimed in claim 10 wherein Z is a moiety M, where M is a gamma emitting moiety for radio or SPECT imaging selected from the group consisting of $^{67}$Ga, $^{111}$In, $^{123}$I, $^{125}$I, $^{131}$I, $^{81m}$Kr, $^{99}$Mo, $^{99m}$Tc, $^{201}$Tl and $^{133}$Xe.

12. An imaging agent as claimed in claim 10 wherein Z is a moiety M, where M is a radio emitter with positron emitting properties for PET imaging selected from the group consisting of $^{11}$C, $^{18}$F, $^{13}$N, $^{15}$O, $^{77}$F, $^{75}$Br, $^{76}$Br, $^{124}$I, $^{64}$Cu, $^{48}$V, $^{52}$Fe, $^{55}$Co, $^{94m}$Tc, $^{68}$Ga or $^{82}$Rb.

13. An imaging agent as claimed in claim 10 wherein Z is a moiety M for MR imaging, where M is selected from the group consisting of a paramagnetic metal selected from the group of Gd(III), Mn(II), Cu(II), Cr(III), Fe(III), Co(II), Er(II), Ni(II), Eu(III) or Dy(III) or a superparamagnetic, ferromagnetic or ferromagnetic metal oxide.

14. An imaging agent as claimed in claim 10 wherein at least either of $Z_1$ and $Z_2$ represent a light scatterer, a light absorber or a light emitter for optical imaging.

15. A pharmaceutical composition comprising the imaging agent of claim 1, together with one or more pharmaceutically acceptable adjuvants, excipients or diluents.

16. A method of generating images of uPAR overexpression in a human or animal body by diagnostic imaging involving administering the imaging agent as claimed in claim 1 to said body, and generating an image of at least a part of said body to which said imaging agent is administered.

\* \* \* \* \*